(12) United States Patent
Mazidji et al.

(10) Patent No.: US 7,837,657 B2
(45) Date of Patent: Nov. 23, 2010

(54) SAFETY DRUG-INJECTING DEVICE WITH TRAVELING HYPODERMIC OR INTRAMUSCULAR NEEDLE

(76) Inventors: George Mazidji, 12 Rue Charles Chabert, 26200 Montelimar (FR); Vera M. Mansour, 3301 Clifden Dr., Tallahassee, FL (US) 32309

( * ) Notice: Subject to any disclaimer, the term of this patent is extended or adjusted under 35 U.S.C. 154(b) by 587 days.

(21) Appl. No.: 11/493,326

(22) Filed: Jul. 26, 2006

(65) Prior Publication Data
US 2008/0097313 A1   Apr. 24, 2008

(51) Int. Cl.
*A61M 5/28*   (2006.01)
(52) U.S. Cl. .............. 604/200; 604/181; 604/187; 604/201; 604/218
(58) Field of Classification Search ............. 604/181, 604/183, 184, 187, 200, 201, 218, 231, 244
See application file for complete search history.

(56) References Cited

U.S. PATENT DOCUMENTS

| | | | |
|---|---|---|---|
| 4,637,934 A * | 1/1987 | White | .......... 426/117 |
| 4,650,468 A | 3/1987 | Jennings, Jr. | |
| 4,664,653 A | 5/1987 | Sagstetter et al. | |
| 4,695,274 A | 9/1987 | Fox | |
| 5,019,043 A | 5/1991 | Segui Pastor et al. | |
| 5,147,303 A | 9/1992 | Martin | |
| 5,370,619 A | 12/1994 | Rossi | |
| 5,647,849 A * | 7/1997 | Kalin | .......... 604/111 |
| 6,537,257 B1 | 3/2003 | Wien | |

* cited by examiner

*Primary Examiner*—Kevin C. Sirmons
*Assistant Examiner*—Bhisma Mehta
(74) *Attorney, Agent, or Firm*—J. Wiley Horton

(57) ABSTRACT

A drug-injecting device with a traveling hypodermic or intramuscular needle. The drug-injecting device includes a syringe body which has a base and a top opening into a hollow interior. A membrane is attached across the base of the syringe body, hermetically sealing the reservoir of the syringe from the environment. A plunger is situated within the hollow interior of the syringe body, so that one end of the plunger projects outward through the top of the syringe body. A piston is attached to the other end of the plunger. The plunger is configured to travel back and forth within the hollow interior of the syringe body between a first position and a second position. A needle is attached to the piston so that the needle travels with the plunger when the plunger is moved between the first and second positions.

10 Claims, 6 Drawing Sheets

SAFETY DRUG-INJECTING DEVICE WITH TRAVELING HYPODERMIC OR INTRAMUSCULAR NEEDLE

BACKGROUND OF THE INVENTION

1. Field of the Invention

This invention relates to the field of drug-injecting devices. More specifically the present invention comprises a drug-injecting device having a traveling hypodermic or intramuscular needle.

2. Description of the Related Art

Infections diseases such as AIDS and hepatitis have led to a growing concern over the safety of drug-injecting devices. Because conventional drug-injecting devices utilize an exposed needle, handling conventional drug-injecting devices carries a risk of accidental disease exposure. For example, it is not uncommon for a person to accidentally prick themselves with the exposed needle while handling the drug-injecting device.

Several inventors have proposed improved injecting devices which would mitigate the risk of accidental disease exposure if the proposed injecting devices were actually used. The designs for these proposed improved injecting devices have been overly complex, making the injecting device expensive to manufacture and/or difficult to use. In addition, prior art syringes are not designed to address the potential risk involved with handling the syringe prior to injection. Instead, prior art "safety syringe" focus on reducing exposure to a contaminated needle after the inoculation has been performed. Accordingly, safety syringes have yet to enjoy widespread acceptance. Thus, there remains a need for an improved drug-injecting device which mitigates the risk of disease exposure while being simple to manufacture and use.

BRIEF SUMMARY OF THE INVENTION

The present invention comprises a drug-injecting device with a traveling needle. The drug-injecting device includes a syringe body which has a base and a top opening into a hollow interior. A membrane is attached across the base of the syringe body, hermetically sealing the reservoir of the syringe from the environment. A plunger is situated within the hollow interior of the syringe body, so that one end of the plunger projects outward through the top of the syringe body. A piston is attached to the other end of the plunger. The plunger is configured to travel back and forth within the hollow interior of the syringe body between a first position and a second position. A needle is attached to the piston so that the needle travels with the plunger when the plunger is moved between the first and second positions.

In the second position, the piston of the plunger is positioned near the base of the syringe so that the needle projects through the membrane. In the first position, the plunger is positioned away from the base of the syringe so that the needle is contained within the reservoir of the syringe body.

The device may be loaded with a drug or other fluid by moving the plunger to the first position and inserting the needle into the fluid to be loaded. The user may then draw the plunger back to the second position where the needle is received within the reservoir. When loaded and positioned in the second position, the needle is immersed in the fluid.

The device may be unloaded, injecting the fluid into an injection site on a person, by moving the plunger from the second position where the needle is contained within the reservoir to said first position where the needle projects through said membrane and into said injection site of said person.

Figure 1:
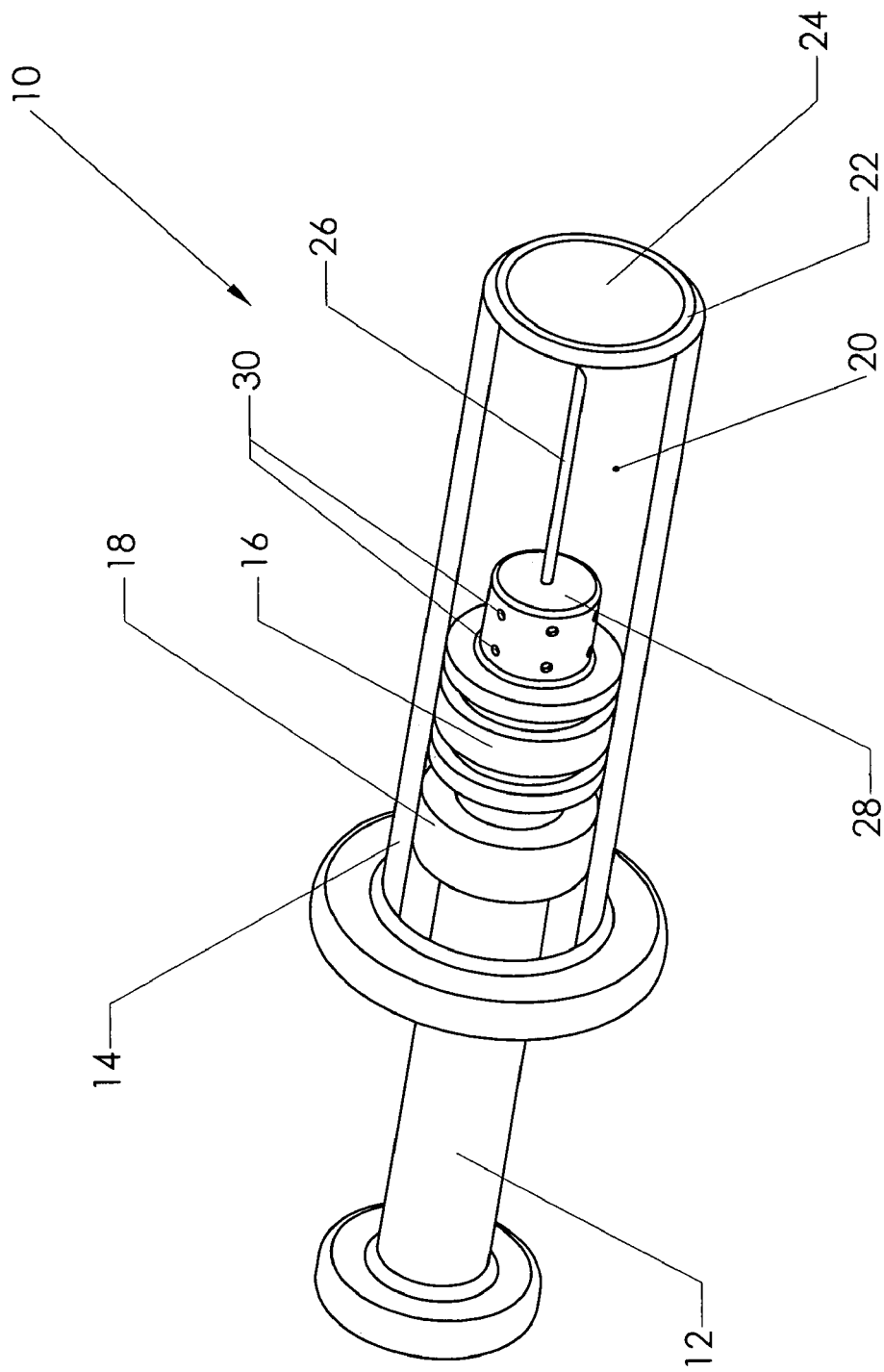
FIG. 1 is a perspective view, showing the present invention.

| REFERENCE NUMERALS IN THE DRAWINGS | |
|---|---|
| 10 | safety syringe |
| 12 | plunger |
| 14 | syringe body |
| 16 | piston |
| 18 | guide |
| 20 | syringe interior |
| 22 | base |
| 24 | membrane |
| 26 | needle |
| 28 | fluid communicator |
| 30 | ports |
| 32 | tip |
| 34 | vial |
| 36 | fluid |
| 38 | interior |
| 40 | reservoir |
| 42 | conduit |
| 44 | injection site |
| 46 | injection surface |

DETAILED DESCRIPTION OF THE INVENTION

The present invention, safety syringe 10 is illustrated in FIG. 1. Safety syringe 10 includes syringe body 14 and plunger 12. Syringe body 14 has base 22 and an open top which opens into hollow syringe interior 20. Membrane 24 is attached to base 22 and hermetically seals syringe interior 20 from the environment. Membrane 24 is preferably made of a performable and resilient material such as rubber, latex, plastic or other polymer. Plunger 12 is insertedly situated within syringe interior 20 such that one of plunger 12 is retained within syringe interior 20 and another end projects outwardly from and through the open top of syringe body 14. Piston 16 is provided on one end of plunger 12. Piston 16 spans across the interior of syringe body 14 from one portion of the sidewall of syringe body 14 to an opposite portion. The portion of syringe interior 20 between piston 16 and membrane 24 acts as a storage reservoir for fluid when safety syringe 10 is loaded as will be explained in greater detail subsequently. Piston 16 hermetically seals the reservoir from the open top of syringe body 14.

Needle 26, a hollow hypodermic or intramuscular needle, is non-releasably attached to piston 16 so that needle 26 travels with plunger 12 when plunger 12 is moved relative to syringe body 14. Needle 26 includes fluid communicator 28 which fluidly connects needle 26 to the reservoir within syringe interior 20. In the preferred embodiment, ports 30 are provided in fluid communicator 28 so that fluid may be exchanged back and forth between needle 26 and the reservoir as will be explained in greater detail subsequently. The needle 26 is attached to the plunger 12 proximal the first end of the plunger 12.

Figure 2:
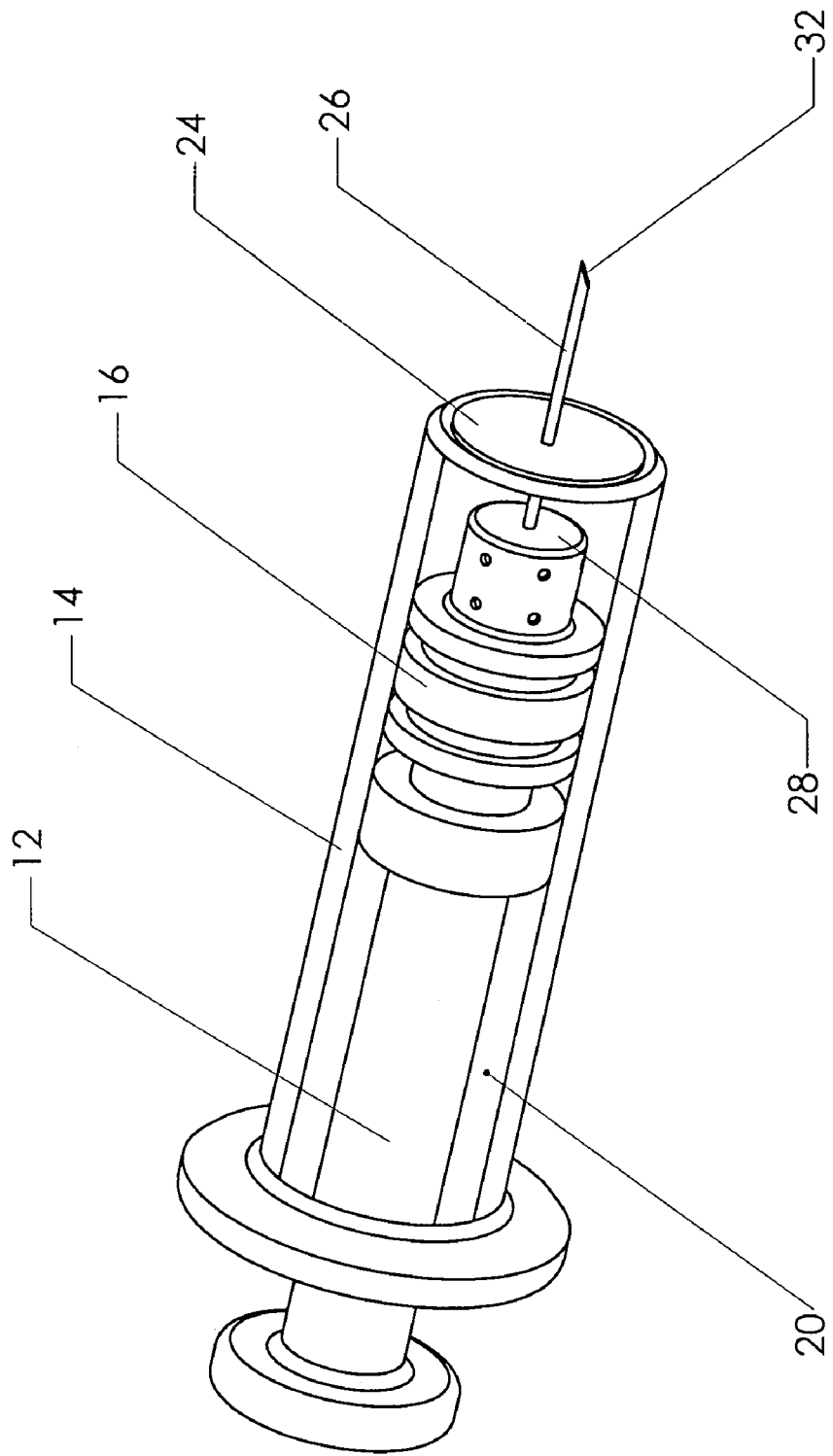
FIG. 2 is a perspective view, showing the present invention.

Plunger 12 is configured to travel back and forth within syringe interior 20 between a first position, as illustrated in FIG. 1 and a second position, as illustrated in FIG. 2. Guide 18 is provided on plunger 12 to maintain the alignment of plunger 12 and needle 26 with respect to syringe body 14 as plunger 12 moves through syringe interior 20. As illustrated in FIG. 1, needle 26 is completely contained within syringe interior 20 when safety syringe 10 is in the first position. As illustrated in FIG. 2, tip 32 of needle 26 projects outward and through membrane 24 when safety syringe 10 is moved to the second position. Fluid communicator 28 arrests the further movement of plunger 12 when fluid communicator 28 mates with the surface of membrane 24. The fluid communicator 28 is proximal the second end of the needle 26. In the first position, the first end of the plunger 12 is distal to the base 22 of the syringe body 14 and, in the second position, the first end of the plunger 12 is proximate to the base 22 of the syringe body 14.

Figure 3:
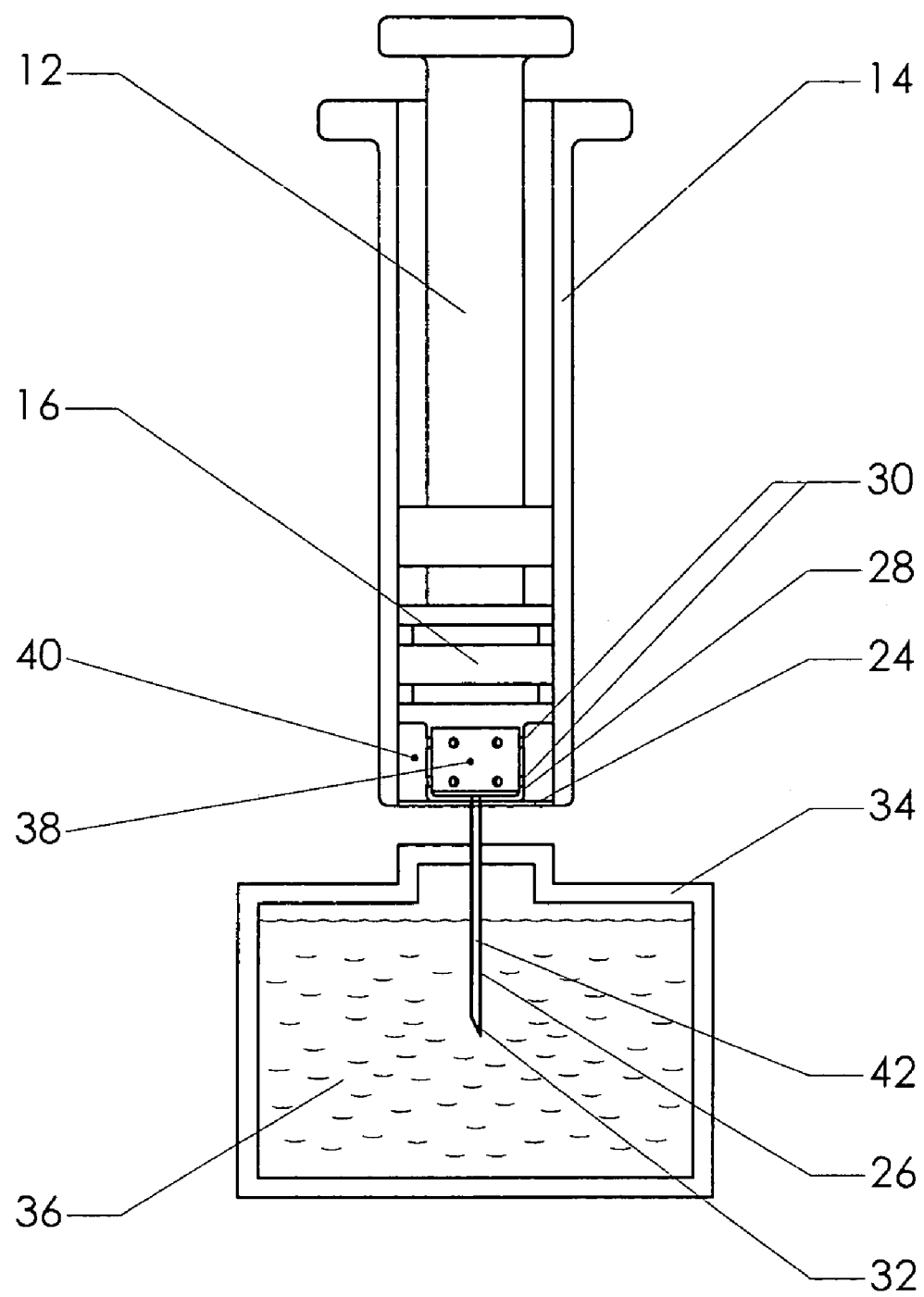
FIG. 3 is a section view, showing the present invention.
Figure 4:
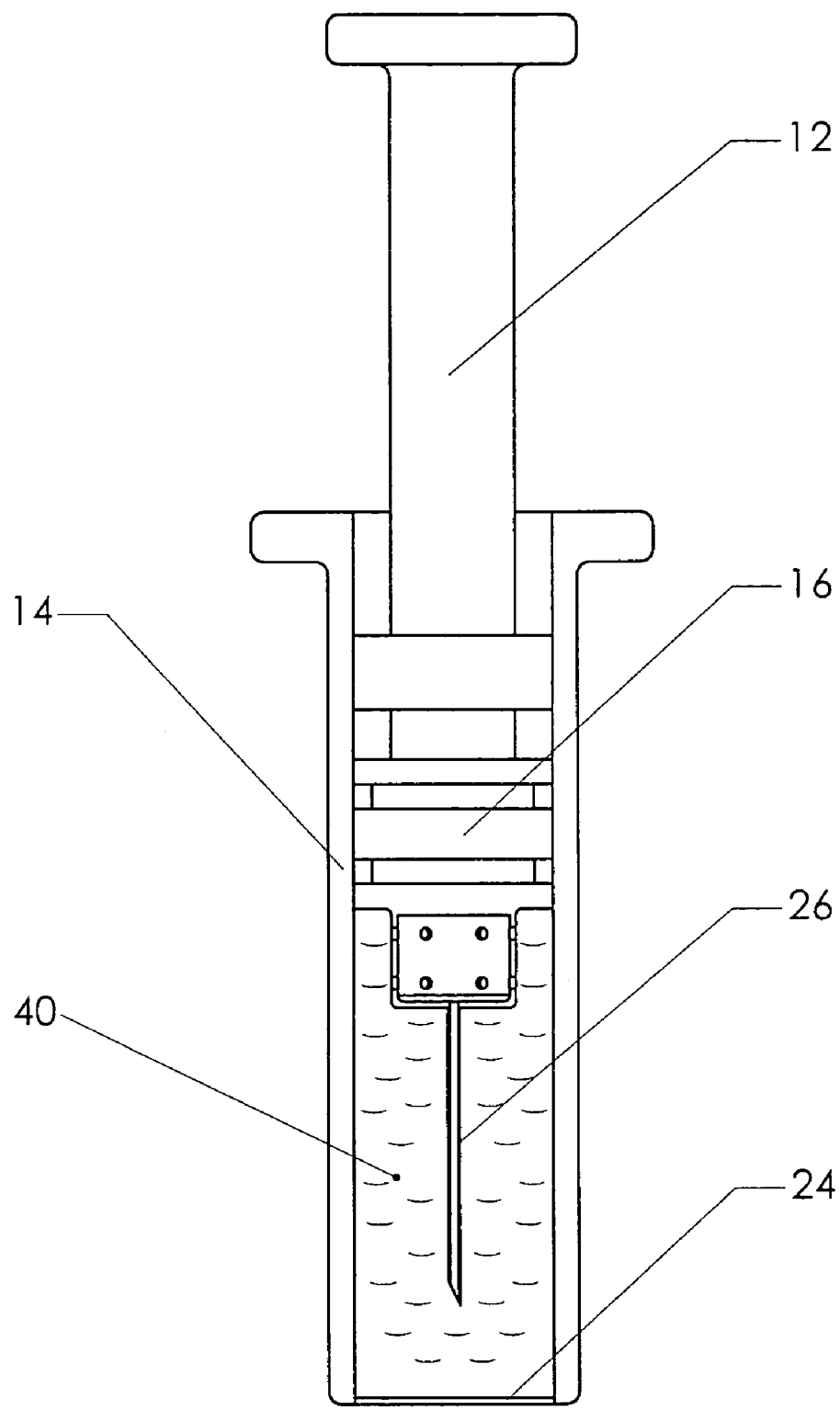
FIG. 4 is a section view, showing the present invention.
Figure 5:
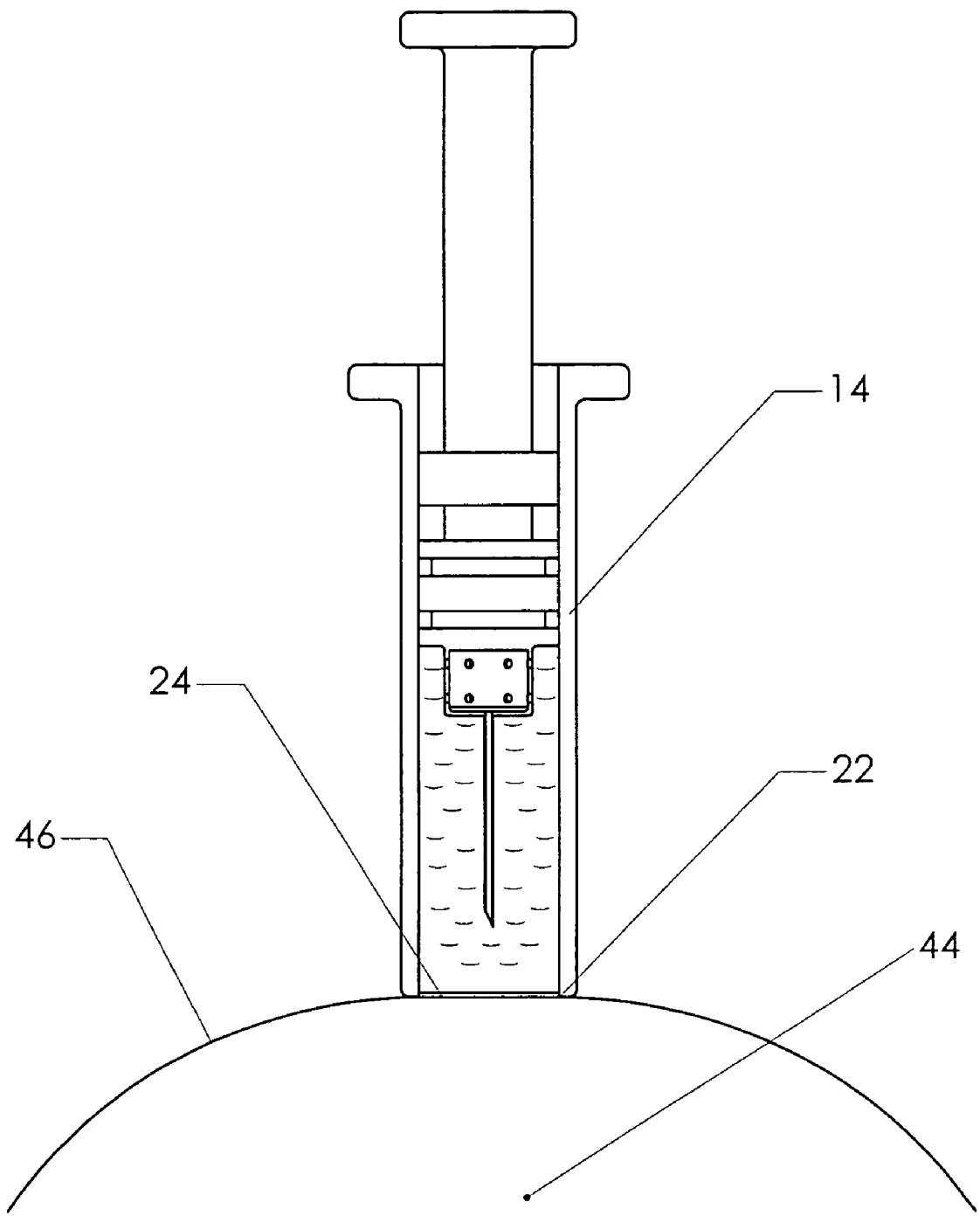
FIG. 5 is a section view, showing the present invention.
Figure 6:
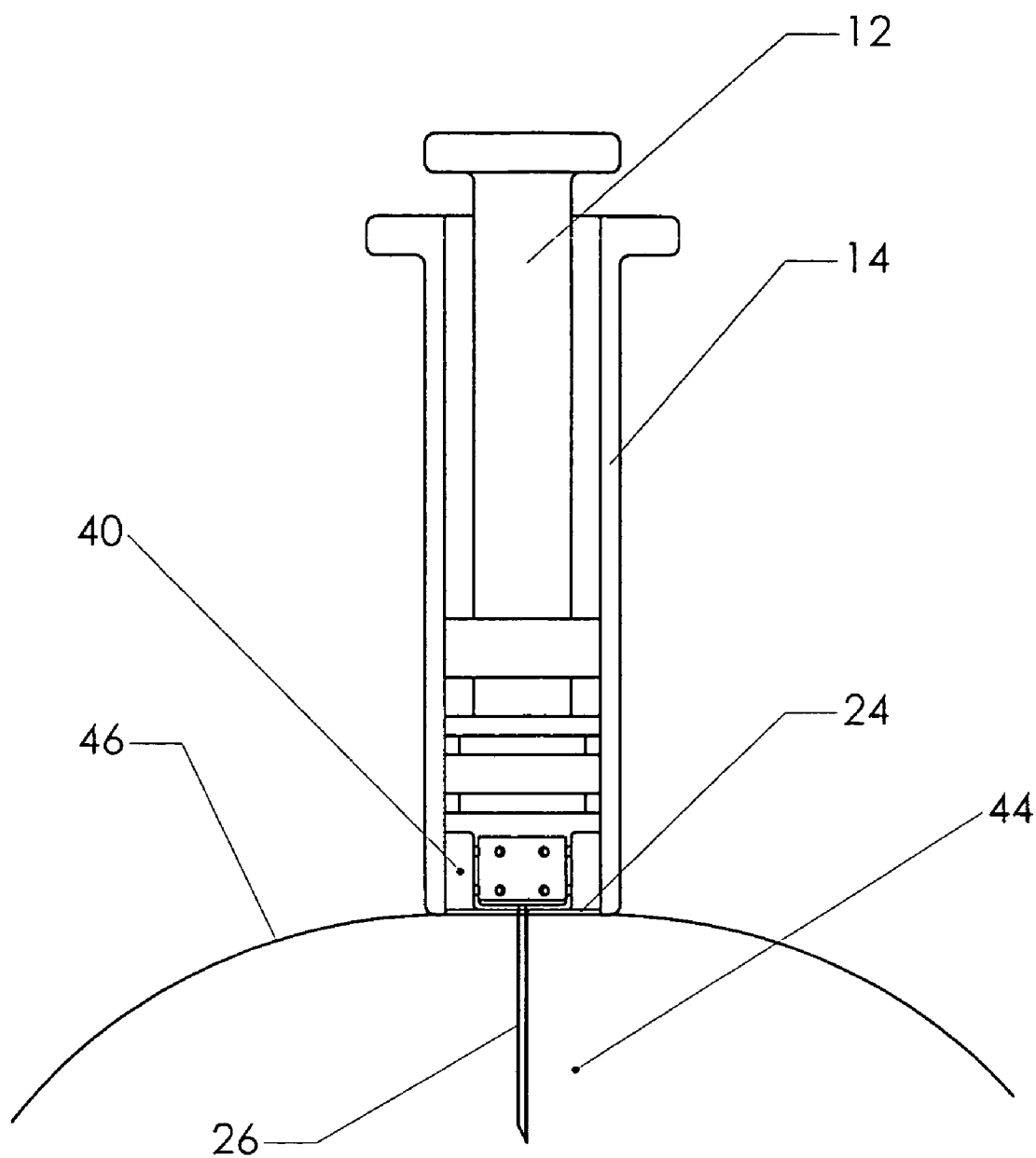
FIG. 6 is a section view, showing the present invention.

The operation of safety syringe 10 is illustrated in FIGS. 3-6. The loading process of safety syringe 10 is illustrated in FIGS. 3 and 4, and the unloading process is illustrated in FIGS. 5 and 6. As illustrated in FIG. 3, the device is loaded by first moving plunger 12 to the second position so that needle 26 projects through membrane 24 and fluid communicator 28 mates with the surface of membrane 24. Tip 32 of needle 26 is submerged into fluid 36 within vial 34. Vial 34 is then inverted to prevent air from being drawn into the syringe. Plunger 12 is then drawn back within syringe body 14, drawing needle 26 back into syringe body 14 therewith. As piston 16 is drawn back within syringe body 14, the volume of reservoir 40 expands, causing a drop in pressure within reservoir 40. This drop in pressure draws fluid 36 through an orifice in tip 32 of needle 26 into conduit 42. From conduit 42, fluid 36 is drawn into interior 38 of fluid communicator 28 and then through ports 30 into reservoir 40.

When plunger 12 is drawn back to the first position, needle 26 is again contained within syringe body 14 as illustrated in FIG. 4. The reader will note that syringe body 14 is immersed in the fluid contained within reservoir 40 when the device is loaded. Membrane 24, being a resilient material, substantially returns to its originally shape and again hermetically seals the contents of reservoir 40 from the environment.

To unload the device, and inject the contents of reservoir 40 into injection site 44, base 22 of syringe body 14 is placed against injection surface 46 as illustrated in FIG. 5. Injection site 44 may be any subcutaneous or intra-muscular location on a person where an injection is needed. Injection surface 46 is the skin above injection site 44. Base 22 is placed against the skin above injection site 44 so that membrane 24 and base 22 mate against injection surface 46. The user then presses plunger 12 into syringe body 14 as shown in FIG. 6. This causes needle 26 to pierce membrane 24 and injection surface 46. As the volume of reservoir 40 decreases, fluid pressure within reservoir 40 increases causing the fluid to be expelled back through needle 26 into injection site 44.

To dispose of safety syringe 10, the user simply draws needle 26 back into syringe body 14 and places the used syringe into an appropriate waste container. The reader will note that throughout the loading process, needle 26 need not be exposed except temporarily when inserting needle 26 into vial 34, as illustrated in FIG. 3. Once the device is loaded, the user may handle the device without significant risk of being pricked by the needle as the needle is safely contained within the interior of syringe body 14.

The preceding description contains significant detail regarding the novel aspects of the present invention. It should not be construed, however, as limiting the scope of the invention but rather as providing illustrations of the preferred embodiments of the invention. As an example, fluid communicator 28 may assume many different shapes or designs. Also, many different types of injection needles may be used. Such variations would not alter the function of the invention. Thus, the scope of the invention should be fixed by the following claims, rather than by the examples given.

We claim:

1. A device for injecting a fluid into an injection site, the injection site beneath an injection surface of a person, comprising:
   a. a syringe body, having a base, a sidewall, a top, said top opening into a hollow interior;
   b. a membrane, attached to said base of said syringe body and closing said base to form said hollow interior;
   c. a plunger, having a first end, and a second end, said first end situated within said hollow interior of said syringe body, and said second end projecting out through said top of said syringe body, said plunger configured to be capable of traveling back and forth within said hollow interior of said syringe body between a first position wherein said first end of said plunger is distal to said base of said syringe body and a second position wherein said first end of said plunger is proximate to said base of said syringe body;
   d. a piston, said piston attached to said first end of said plunger, said piston configured to span said hollow interior of said syringe body;
   e. a reservoir for holding the fluid within said hollow interior of said syringe body, said reservoir formed between said piston, said membrane, and said sidewall of said syringe body, said reservoir hermetically sealed;
   f. a needle, attached to said plunger proximal said first end of said plunger, said needle configured to travel with said plunger when said plunger moves between said first position and said second position, said needle having a first end and a second end, said needle including
      i. a tip, proximal said first end of said needle, said tip configured to pierce the skin of the person, said tip having an orifice;
      ii. a fluid communicator, proximal said second end of said needle, said fluid communicator fluidly connecting said needle to said reservoir;
      iii. a conduit fluidly connecting said orifice to said fluid communicator, with said fluid communicator being fluidly connected to said reservoir;
   g. wherein said tip of said needle is configured to project through said membrane and outside of said reservoir when said plunger is moved to said second position, and wherein said tip of said needle is positioned within said reservoir when said plunger is moved to said first position; and
   h. wherein said tip of said needle is immersed in the fluid contained within said reservoir when said device is loaded and said plunger is moved to said first position.

2. The device of claim 1, wherein said device is configured to load the fluid into said reservoir by
   a. moving said plunger to said second position and inserting said needle in the fluid in a separate vial; and
   b. drawing said plunger back to said first position where said needle is received within said reservoir.

3. The device of claim 1, wherein said fluid communicator further comprised a plurality of ports, each of said ports configured to fluidly connect said needle to said reservoir.

4. The device of claim 1, wherein said needle is non-releasably attached to said plunger so that said needle travels with said plunger as said plunger is cyclically moved between said first position and said second position.

5. The device of claim 1, wherein said device is configured to be unloaded, injecting the fluid into the injection site of the person by:
   a. pressing said base of said syringe body against the injection surface so that said base of said syringe and said membrane mate against the injection surface; and
   b. moving said plunger from said first position where said needle is contained within said reservoir to said second position where said needle projects through said membrane and into the injection site of the person.

6. A device for injecting a fluid into an injection site, the injection site beneath an injection surface of a person, comprising:
   a. a syringe body, having a base and a top opening into a hollow interior;
   b. a plunger, having a first end and a second end, said first end situated within said hollow interior of said syringe body, and said second end projecting out through said top of said syringe body, said plunger moveable between a second position wherein said first end of said plunger is proximal said base of said syringe body and a first position wherein said first end of said plunger is distal said base of said syringe body;
   c. a needle, said needle attached to said first end of said plunger such that said needle travels with said plunger when said plunger moves between said first position and said second position;
   d. a membrane, attached to said base of said syringe body and closing said base to form said hollow interior;
   e. a reservoir holding the fluid within said hollow interior of said syringe body, said reservoir formed within said hollow interior of said syringe body between said first end of said plunger and said membrane, said reservoir hermetically sealed;
   f. wherein said tip of said needle is configured to project through said membrane and outside of said reservoir when said plunger is moved to said second position, and wherein said tip of said needle is positioned within said reservoir when said plunger is moved to said first position; and
   g. wherein said device is configured to load the fluid into said reservoir by
      i. moving said plunger to said second position and inserting said needle in the fluid in a separate vial; and
      ii. drawing said plunger back to said first position until said needle is received within said reservoir.

7. The device of claim 6, said needle having a first end and a second end, said needle including
   i. said tip, proximal said first end of said needle, said tip configured to pierce the skin of the person, said tip having an orifice;
   ii. a fluid communicator, proximal said second end of said needle, said fluid communicator fluidly connecting said needle to said reservoir; and
   iii. a conduit fluidly connecting said orifice to said fluid communicator.

8. The device of claim 7, wherein said fluid communicator further comprised a plurality of ports, each of said ports configured to fluidly connect said needle to said reservoir.

9. The device of claim 6, wherein said needle is non-releasably attached to said plunger so that said needle travels with said plunger as said plunger is cyclically moved between said first position and said second position.

10. The device of claim 6, wherein said device is configured to be unloaded, injecting the fluid into the injection site of the person by:
   a. pressing said base of said syringe body against the injection surface so that said base of said syringe and said membrane mate against the injection surface; and
   b. moving said plunger from said first position where said needle is contained within said reservoir to said second position where said needle projects through said membrane and into the injection site of the person.

* * * * *